(12) United States Patent
Asada et al.

(10) Patent No.: US 8,224,060 B2
(45) Date of Patent: Jul. 17, 2012

(54) IMAGE PROCESSING METHOD, PAINT INSPECTION METHOD AND PAINT INSPECTION SYSTEM

(75) Inventors: Yasunori Asada, Okazaki (JP); Norio Miyazato, Sagamihara (JP); Eiji Yamazaki, Kazo (JP)

(73) Assignee: Toyota Jidosha Kabushiki Kaisha, Toyota-shi, Aichi-ken (JP)

( * ) Notice: Subject to any disclaimer, the term of this patent is extended or adjusted under 35 U.S.C. 154(b) by 465 days.

(21) Appl. No.: 12/574,807

(22) Filed: Oct. 7, 2009

(65) Prior Publication Data

US 2010/0092069 A1    Apr. 15, 2010

(30) Foreign Application Priority Data

Oct. 10, 2008    (JP) ................................. 2008-264105

(51) Int. Cl.
*G06K 9/00*    (2006.01)
*G01N 21/88*    (2006.01)
(52) U.S. Cl. ..................... 382/141; 356/237.2
(58) Field of Classification Search .................. 382/141, 382/145, 149, 154, 286; 356/237.1–237.4, 356/394; 250/559.22, 559.48; 702/81, 20, 702/35
See application file for complete search history.

(56) References Cited

U.S. PATENT DOCUMENTS

| | | | | |
|---|---|---|---|---|
| 5,625,197 A | * | 4/1997 | Shimbara | 250/559.22 |
| 5,822,054 A | * | 10/1998 | Coulthard | 356/237.2 |
| 6,055,325 A | * | 4/2000 | Garini et al. | 382/129 |
| 6,510,355 B1 | * | 1/2003 | Hollenbeck et al. | 700/95 |
| 6,714,831 B2 | * | 3/2004 | Matthews et al. | 700/110 |
| 6,826,497 B1 | * | 11/2004 | Collins | 702/81 |
| 2007/0229810 A1 | * | 10/2007 | Kaya | 356/237.2 |
| 2008/0063254 A1 | * | 3/2008 | Tanizaki et al. | 382/141 |

FOREIGN PATENT DOCUMENTS

| | | | |
|---|---|---|---|
| JP | 5-223548 | | 8/1993 |
| JP | 7-200819 | | 8/1995 |
| JP | 8-168004 | | 6/1996 |
| JP | 11023243 A | * | 1/1999 |
| JP | 2002-22668 | | 1/2002 |
| JP | 2004-69673 | | 3/2004 |
| JP | 2004-303075 | | 10/2004 |
| JP | 2008-249397 | | 10/2008 |

OTHER PUBLICATIONS

Notification of Reason(s) for Refusal for JP 2008-264105 dated Jul. 13, 2010.

* cited by examiner

*Primary Examiner* — Sang Nguyen
(74) *Attorney, Agent, or Firm* — Finnegan, Henderson, Farabow, Garrett & Dunner, LLP

(57) ABSTRACT

An image processing method that differentiates image data using an image processing system that includes a processing unit and a storage unit includes: acquiring image data; sequentially picking up pixels one by one at a predetermined pitch from among the pixels that constitute the image data and setting the picked up pixels as reference pixels; setting a close region around each of the reference pixels; calculating an average value of densities of the picked up pixels for each of the close regions; setting a wide region larger than the close region around each of the reference pixels; calculating an average value of densities of the picked up pixels for each of the wide regions; and calculating a difference between the density of each of the reference pixels and a corresponding one of the average values of the densities of the pixels of the wide regions.

10 Claims, 9 Drawing Sheets

| | | | | | | | | | |
|---|---|---|---|---|---|---|---|---|---|
| 200 | 200 | 200 | 200 | 200 | 200 | 200 | 200 | 200 | ← 701 |
| 200 | 200 | 200 | 200 | 200 | 200 | 200 | 200 | 200 | |
| 200 | 200 | 200 | 200 | 200 | 200 | 200 | 200 | 200 | |
| 200 | 200 | 200 | 200 | 200 | 200 | 200 | 200 | 200 | |
| 200 | 200 | 200 | 200 | 200 | 200 | 200 | 200 | 200 | |
| 200 | 200 | 200 | 200 | 10 | 200 | 200 | 200 | 200 | ← 711 |
| 200 | 200 | 200 | 200 | 200 | 200 | 200 | 200 | 200 | |
| 200 | 200 | 200 | 200 | 200 | 200 | 200 | 200 | 200 | |
| 200 | 200 | 200 | 200 | 200 | 200 | 200 | 200 | 200 | |
| 200 | 200 | 200 | 200 | 200 | 200 | 200 | 200 | 200 | |
| 200 | 200 | 200 | 200 | 200 | 200 | 200 | 200 | 200 | |
| 200 | 200 | 200 | 200 | 200 | 200 | 200 | 200 | 200 | |

IMAGE PROCESSING METHOD, PAINT INSPECTION METHOD AND PAINT INSPECTION SYSTEM

INCORPORATION BY REFERENCE

The disclosure of Japanese Patent Application No. 2008-264105 filed on Oct. 10, 2008, including the specification, drawings and abstract is incorporated herein by reference in its entirety.

BACKGROUND OF THE INVENTION

1. Field of the Invention

The invention relates to an image processing method that differentiates an image signal and further to a paint inspection method and paint inspection system that use the image processing method.

2. Description of the Related Art

An image signal acquired through an image pickup device may include an image portion that a user wants to keep and an image portion that is unnecessary for the user depending on the application of the image signal. The image portion that is unnecessary for the user has a large density change with respect to the surroundings. Thus, by detecting a portion having a large density change, it is possible to detect the image portion that is unnecessary for the user. Then, if the image portion that is unnecessary for the user may be detected, it is only necessary that the unnecessary image portion is removed.

Japanese Patent Application Publication No. 8-168004 (JP-A-8-168004) describes a method of forming a high-quality image close to an original picture by forming an appropriate edge for an image degraded because of noise, or the like. Japanese Patent Application Publication No. 2004-303075 (JP-A-2004-303075) describes an image processing technique for reducing low-frequency noise and high-frequency noise.

A known technique for calculating a density change includes Sobel filter, median filter, or the like. However, these techniques may possibly detect not only an image portion that the user wants to keep but also an unnecessary image portion.

SUMMARY OF THE INVENTION

The invention provides an image processing method that keeps an image portion that is necessary for a user and that removes an image portion that is unnecessary for the user, and a paint inspection method and paint inspection system that use the image processing method.

A first aspect of the invention relates to an image processing method. In the image processing method, first, pixels are sequentially picked up one by one at a predetermined pitch from among pixels that constitute original image data. These are defined as reference pixels ai (i=1 to k). Subsequently, a close region is set for each reference pixel, and an average value of similar densities in each close region is calculated. After that, a wide region is set for each reference pixel, and an average value of similar densities in each wide region is calculated. Lastly, the average value of similar densities in each wide region is subtracted from the image data of the original image to obtain a difference therebetween.

More specifically, the image processing method according to the first aspect relates to a method of differentiating image data using an image processing system that includes a processing unit and a storage unit. The image processing method includes: an image data acquisition step; a reference pixel acquisition step; a close region setting step; a first similar density acquisition step; a first similar density average calculation step; a wide region setting step; a second similar density acquisition step; a second similar density average calculation step; and an average difference calculation step. The image data acquisition step acquires image data, which include a density of each pixel acquired by an image pickup apparatus, using the processing unit. The reference pixel acquisition step sequentially picks up pixels one by one at a predetermined pitch from among the pixels that constitute the image data and setting the picked up pixels as reference pixels (i=1 to k). The close region setting step sets a predetermined region around each of the reference pixels ai (i=1 to k) as a close region Ai. The first similar density acquisition step picks up a predetermined number of pixels having a small difference in density with respect to the density of a corresponding one of the reference pixels in increasing order of a difference in density from among the pixels included in each close region Ai, using the processing unit. The first similar density average calculation step calculates an average value of densities of the pixels picked up in the first similar density acquisition step for each of the close regions, using the processing unit. The wide region setting step sets a predetermined region larger than the close region around each of the reference pixels (i=1 to k) as a wide region Bi. The second similar density acquisition step picks up a predetermined number of pixels having a small difference in density with respect to a corresponding one of the average values calculated in the first similar density average calculation step in increasing order of a difference in density from among the pixels included in each of the wide regions Bi, using the processing unit. The second similar density average calculation step calculates an average value of densities of the pixels picked up in the second similar density acquisition step for each of the wide regions, using the processing unit. The average difference calculation step calculates a difference between the density of each of the reference pixels and a corresponding one of the average values calculated in the second similar density average calculation step, using the processing unit.

A second aspect of the invention relates to a paint inspection method. The paint inspection method includes: a step of irradiating illumination light to a vehicle body by a lighting unit; a step of picking up a digital image of the vehicle body by an image pickup apparatus; a step of differentiating the digital image of the vehicle body by an image processing system that includes a processing unit and a storage unit; and a step of detecting a paint defect using the differentiated image data. In the paint inspection method, the differentiating step includes an image data acquisition step; a reference pixel acquisition step; a close region setting step; a first similar density acquisition step; a first similar density average calculation step; a wide region setting step; a second similar density acquisition step; a second similar density average calculation step; and an average difference calculation step. The image data acquisition step acquires image data, which include a density of each pixel acquired by an image pickup apparatus, using the processing unit. The reference pixel acquisition step sequentially picks up pixels one by one at a predetermined pitch from among the pixels that constitute the image data and setting the picked up pixels as reference pixels (i=1 to k). The close region setting step sets a predetermined region around each of the reference pixels ai (i=1 to k) as a close region Ai. The first similar density acquisition step picks up a predetermined number of pixels having a small difference in density with respect to the density of a corresponding one of the reference pixels in increasing order of a difference in density from among the pixels included in each close region Ai, using the processing unit. The first similar density average calculation step calculates an average value of densities of the pixels picked up in the first similar density acquisition step for each of the close regions, using the processing unit. The wide region setting step sets a predetermined region larger than the close region around each of the reference pixels (i=1 to k) as a wide region Bi. The second similar density acquisition step picks up a predetermined number of pixels having a small difference in density with respect to a corresponding one of the average values calculated in the first similar density average calculation step in increasing order of a difference in density from among the pixels included in each of the wide regions Bi, using the processing unit. The second similar density average calculation step calculates an average value of densities of the pixels picked up in the second similar density acquisition step for each of the wide regions, using the processing unit. The average difference calculation step calculates a difference between the density of each of the reference pixels and a corresponding one of the average values calculated in the second similar density average calculation step, using the processing unit.

A third aspect of the invention relates to a paint inspection system. The paint inspection system includes: a lighting unit that irradiates illumination light to a vehicle body; an optical system that magnifies or reduces an image of the vehicle body; an image pickup apparatus that picks up a digital image of the vehicle body; and an image processing system that detects a paint defect from the digital image of the vehicle body. In addition, the image processing system includes a storage unit, a processing unit and a memory. In the paint inspection system, the processing unit acquires image data, which include a density of each pixel, from the image pickup device and differentiates the image data. The differentiation executed by the processing unit includes acquiring the image data which include the density of each pixel acquired by the image pickup apparatus; sequentially picking up pixels one by one at a predetermined pitch from among the pixels that constitute the image data and setting the picked up pixels as reference pixels ai (i=1 to k); setting a predetermined region around each of the reference pixels (i=1 to k) as a close region Ai; picking up a predetermined number of pixels having a small difference in density with respect to the density of a corresponding one of the reference pixels in increasing order of a difference in density from among the pixels included in each of the close regions Ai; and calculating an average value of densities of the picked up pixels as a first average value for each of the close regions Ai. The differentiation further includes setting a predetermined region larger than the close region around each of the reference pixels (i=1 to k) as a wide region Bi; and picking up a predetermined number of pixels having a small difference in density with respect to a corresponding one of the first average values in increasing order of a difference in density from among the pixels included in each of the wide regions Bi. The differentiation additionally includes calculating an average value of densities of the picked up pixels as a second average value for each of the wide regions. Then, the differentiation includes calculating a difference between the density of each of the reference pixels and a corresponding one of the second average values.

With the image processing method, paint inspection method and paint inspection system according to the aspects of the invention, it is possible to keep an image portion necessary for a user and remove an unnecessary image portion through differentiation.

BRIEF DESCRIPTION OF THE DRAWINGS

The features, advantages, and technical and industrial significance of this invention will be described in the following detailed description of example embodiments of the invention with reference to the accompanying drawings, in which like numerals denote like elements, and wherein.

DETAILED DESCRIPTION OF EMBODIMENTS

Figure 1:
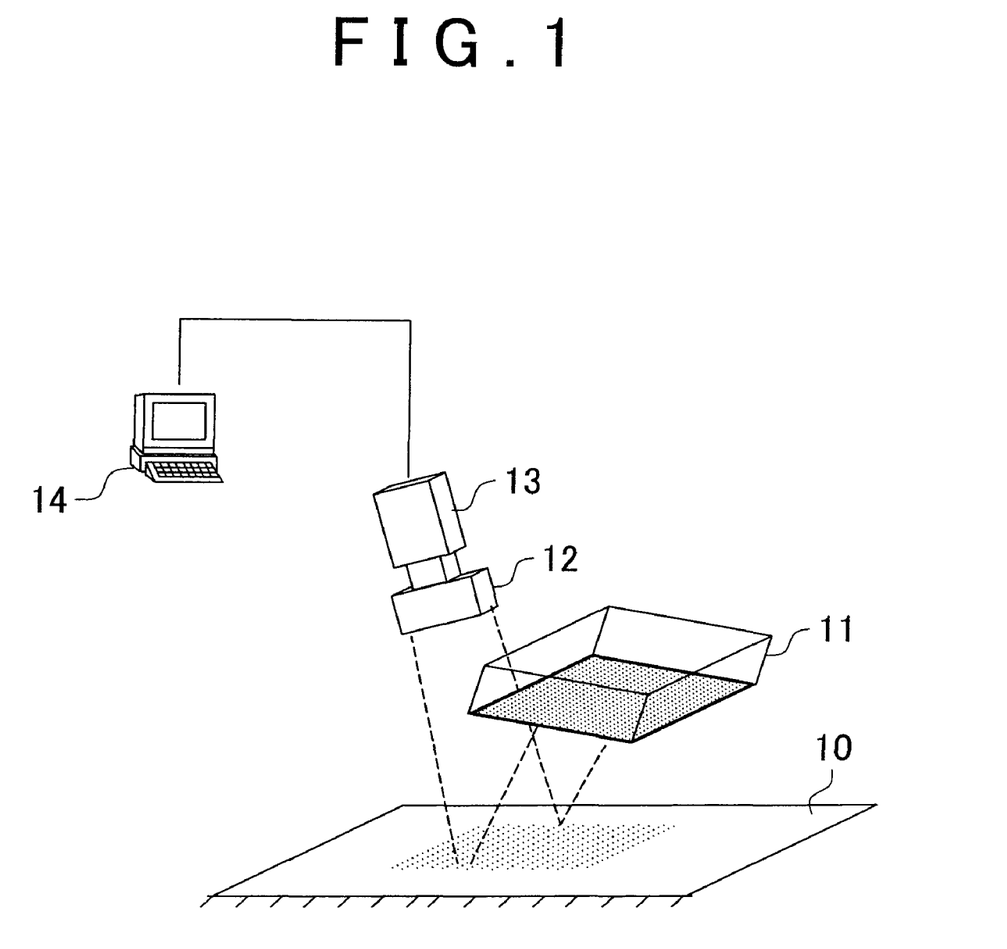
FIG. 1 is a schematic view of a paint inspection system for the body of a vehicle according to an embodiment of the invention.

The overview of a method of inspecting the paint of the body of a vehicle will be described with reference to FIG. 1. A paint inspection system includes a lighting unit 11, an optical system (lens unit) 12, a camera 13 and an image processing apparatus 14. The lighting unit 11 irradiates illumination light to the body 10 of the vehicle. The optical system 12 magnifies or reduces an image of the vehicle body. The camera 13 picks up a digital image of the vehicle body. The image processing system 14 detects a paint defect from the digital image of the vehicle body. The camera 13 may be a CCD camera. The image processing system 14 may be a typical computer that includes a storage unit, a processing unit and a memory. Such a computer is equipped with an input device, a display device and a printer. The paint inspection system according to the present embodiment divides the surface of the body of a vehicle into small regions, and automatically inspects paint in each region. The paint inspection system is installed in a robot (not shown) and moves around the body of the vehicle.

Figure 2:
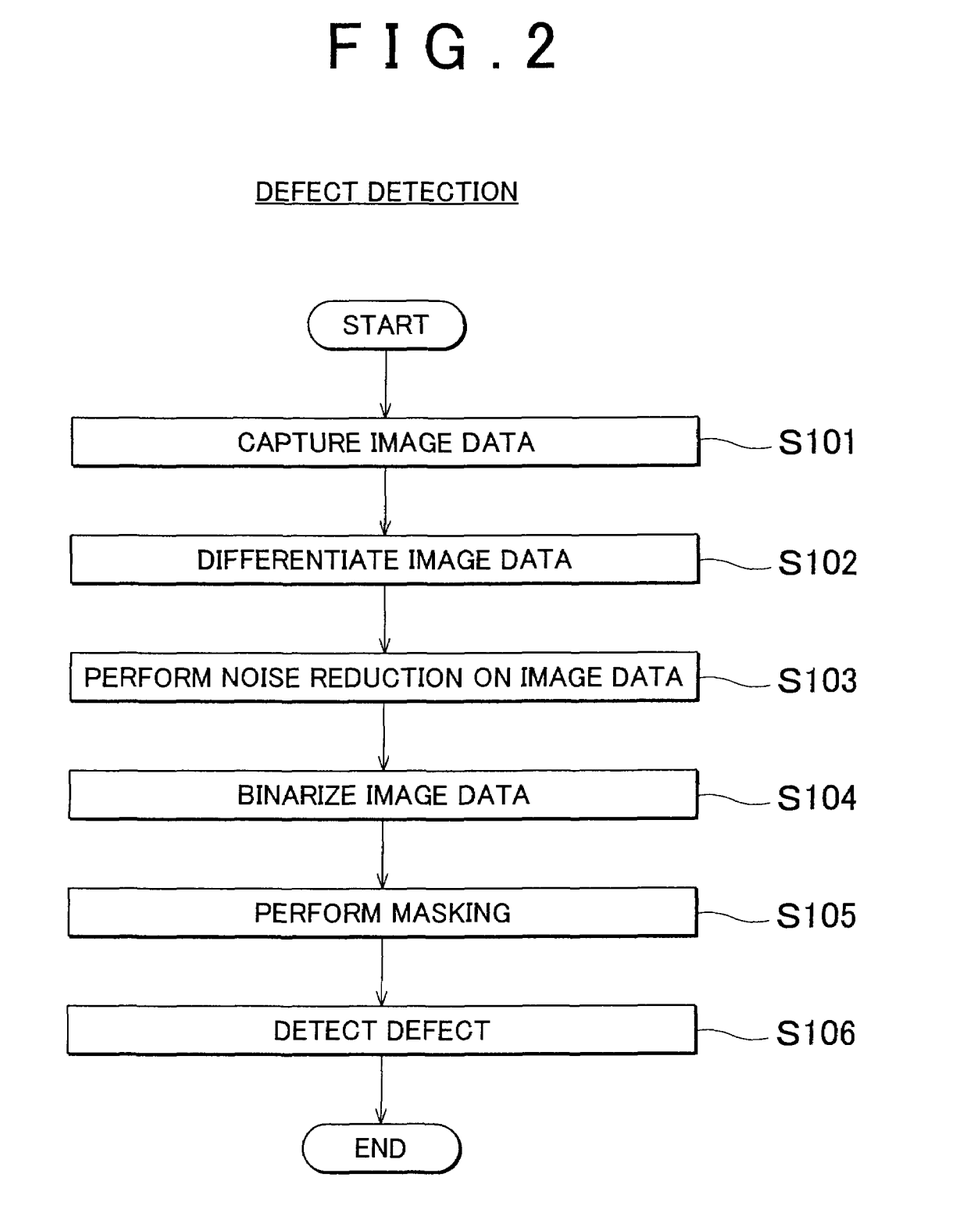
FIG. 2 is a flowchart that shows the overview of a process of detecting a paint defect by the paint inspection system for the body of a vehicle according to the embodiment of the invention.

The procedure of a process of detecting a paint defect by the image processing system will be described with reference to FIG. 2. First, in step S101, the processing unit of the image processing system 14 captures image data from the camera, and stores the image data in the memory or the storage unit. In step S102, the processing unit differentiates the image data. By so doing, density changes in the image data may be obtained. A region having a large density change may be a defect; however, the region may not be a defect. Edges of doors, door knobs, window glasses, head lamps, and the like, have a large density change. The differentiation according to the embodiment of the invention removes image portions having a large density change other than a defect. Thus, it is possible to efficiently detect a defect. The differentiation will be described in detail later with reference to FIG. 4. In step S103, the processing unit performs noise reduction on the image data. The noise reduction smoothes the image data. In step S104, the processing unit binarizes the image data. By so doing, the image is classified into two regions, that is, a region having a high density and a region having a low density. For example, the image is classified into a black region and a white region. From the binarized image, it is possible to detect a candidate for a defect. For example, the white region is determined to be a candidate for a defect. In step S105, the processing unit performs masking. That is, mask areas are removed from the binarized image. The door knobs, window glasses, head lamps, and the like, are not painted, so they are mask areas. Lastly, in step S106, the processing unit detects a defect. The defect candidate detected in step S104, other than the mask areas, is determined to be a paint defect.

Figure 3:
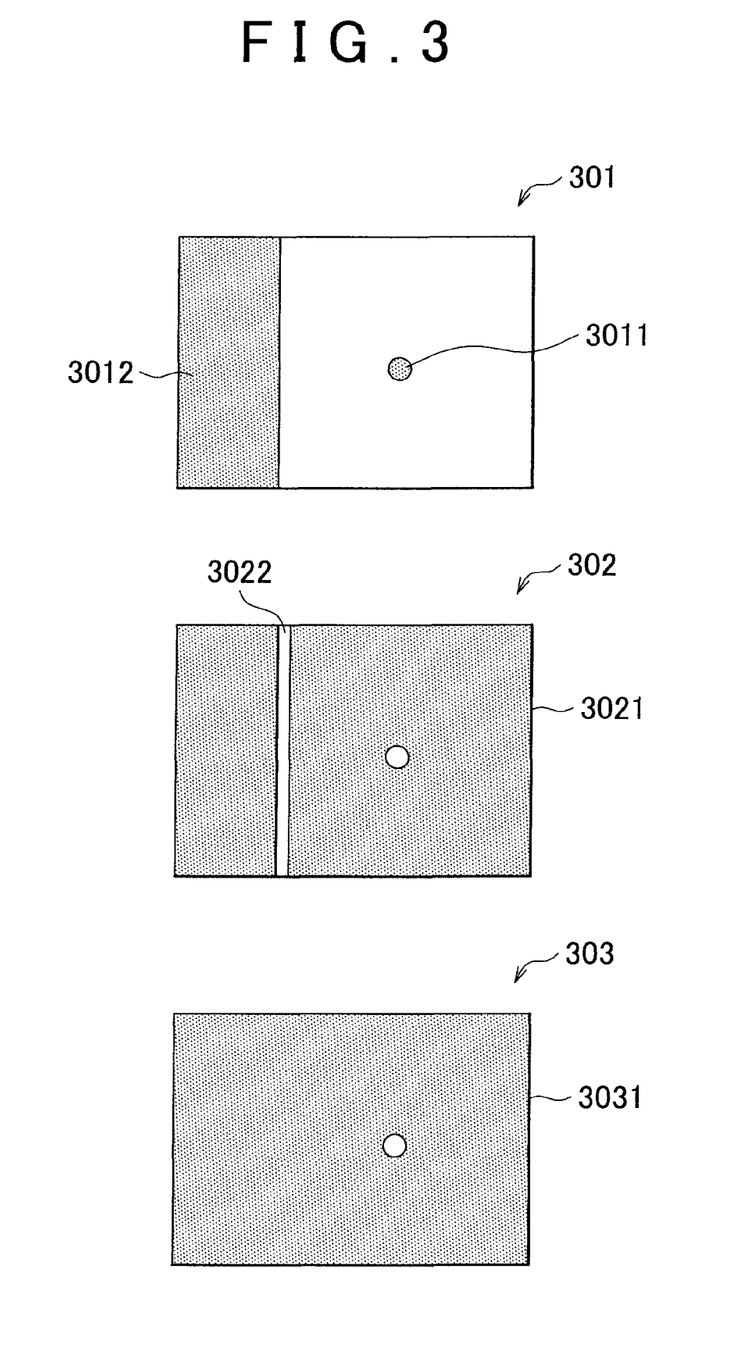
FIG. 3 is a view that shows examples of images in the paint inspection system for the body of a vehicle according to the embodiment of the invention.

FIG. 3 shows an original image 301 captured from the camera and examples of differentiated and binarized images 302 and 303. The original image 301 includes an image region that a user wants to keep, that is, a paint defect 3011 and an image region 3012 that the user wants to remove. The image region 3012 that the user wants to remove is, for example, a door knob, a window glass, a head lamp, or the like. The edge of the image region 3012 that the user wants to remove has a large density change. An edge of the image region 3012 that the user wants to remove, that is, a region 3022 having a large density change, remains in the image 302 differentiated in accordance with the related art of the invention. Thus, when a paint defect 3021 is detected, there is a possibility that erroneous detection may occur. In an image 303 differentiated in accordance with the embodiment of the invention, the edge of the image region 3012 that the user wants to remove has been removed. Thus, erroneous detection does not occur when a paint defect 3031 is detected.

A differentiation method according to the embodiment of the invention will be described with reference to FIG. 4. In step S201, the processing unit of the image processing system 14 sequentially picks up pixels one by one at a predetermined pitch from pixels that constitute original image data. These are defined as reference pixels ai (i=1 to k). The densities of these reference pixels are denoted by pi (i=1 to k). When the pitch is one pixel, all the pixels are sequentially picked up. The order of picking up pixels may be the order of scanning the pixels that constitute pixel data. In step S202, the processing unit sets a close region for each reference pixel, and calculates the average value of similar densities in each close region. A method of calculating the average value of similar densities in each close region will be described in detail later with reference to FIG. 5.

In step S203, the processing unit sets a wide region for each reference pixel, and calculates the average value of similar densities in each wide region. A method of calculating the average value of similar densities in each wide region will be described in detail later with reference to FIG. 6. Lastly, in step S204, the processing unit subtracts the average values of similar densities in the respective wide regions from the image data of the original image to obtain differences therebetween. In the thus obtained difference data, the edge of the image region 3012 that the user wants to remove in the original image 301 is removed, and only the image region that the user wants to keep, that is, only the paint defect, remains.

The method of calculating the average value of similar densities in each close region in step S202 of FIG. 4 will be described with reference to FIG. 5. In step S301, the processing unit sets a predetermined region around each of the reference pixels ai (i=1 to k). These are denoted by close regions Ai (i=1 to k). The number of pixels included in each of the close regions Ai is desirably equal among all the close regions. However, when the reference pixel is located at an edge of the image, the number of pixels included in the close region may be smaller than that.

In step S302, the processing unit picks up a predetermined number of pixels having a small difference in density with respect to the density pi of the reference pixel ai in increasing order of a difference in density from among the pixels included in each of the close regions Ai. That is, pixels having similar densities with respect to the density pi of each reference pixel ai are picked up. For example, it is assumed that n pixels cij (j=1 to n, where n is equal to or smaller than the number of pixels included in each close region Ai) are picked up. In step S303, the processing unit calculates the average value of the densities of the n pixels cij (j=1 to n). The average values of the densities are denoted by cmi (i=1 to k). This is the average value of similar densities in each close region.

Figure 6:
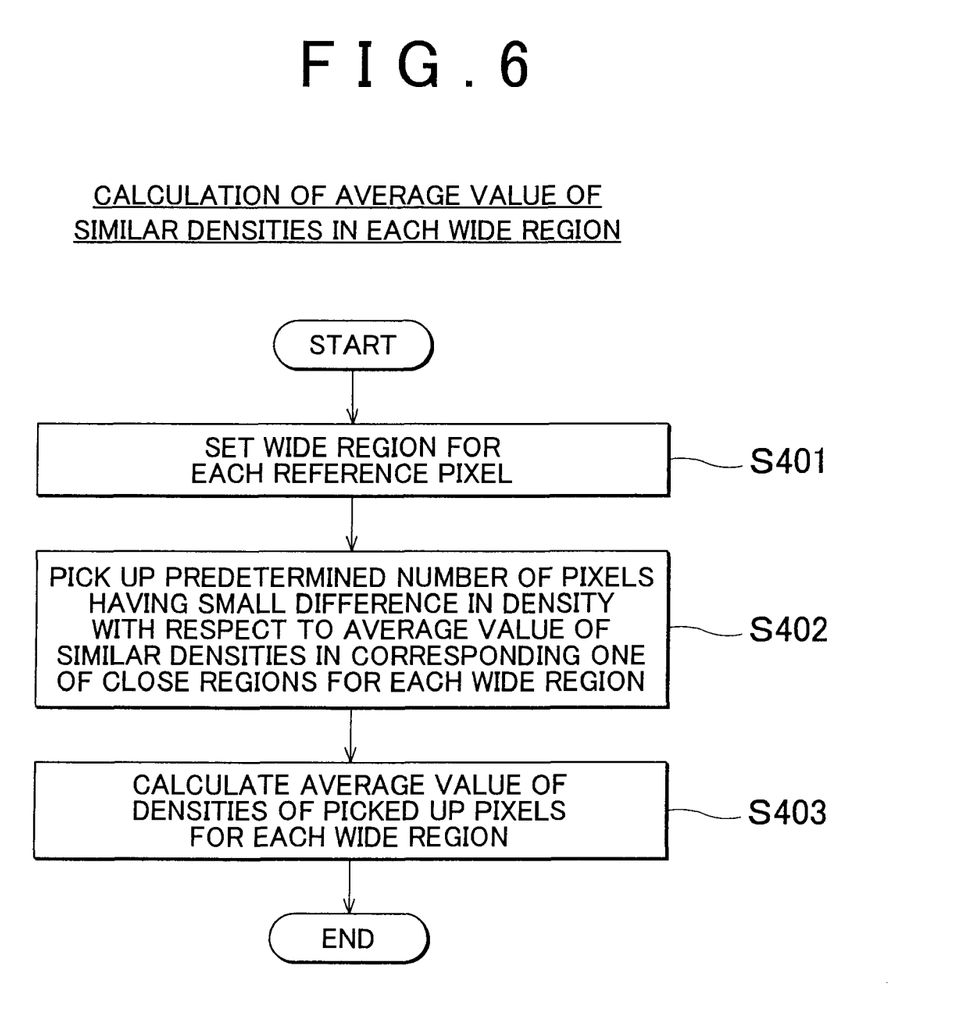
FIG. 6 is a view that shows the overview of a process of calculating an average value of similar densities in each wide region in the differentiation according to the embodiment of the invention.

The method of calculating the average value of similar densities in each wide region in step S203 of FIG. 4 will be described with reference to FIG. 6. In step S401, the processing unit sets a predetermined region around each of the reference pixels bi (i=1 to k). These are denoted by wide regions Bi (i=1 to k). However, the wide regions Bi set here are larger than the close regions Ai set in step S301. The number of pixels included in each wide region Bi is desirably equal among all the wide regions. However, when the reference pixel is located at an edge of the image, the number of pixels included in the wide region may be smaller than that.

In step S402, the processing unit picks up a predetermined number of pixels having a small difference in density with respect to the average values of similar densities in a corresponding one of the close regions in increasing order of a difference in density from among the pixels included in each of the wide regions Bi. That is, pixels having similar densities with respect to the average value cmi of similar densities in each closer region are picked up. For example, it is assumed that m pixels cij (j=1 to m, where m is smaller than the number of pixels included in each region Bi) are picked up. In step S403, the processing unit calculates the average value of the densities of the m pixels cij (j=1 to m). The average values of the densities are denoted by cami (i=1 to k). This is the average value of similar densities in each wide region.

Figure 7:
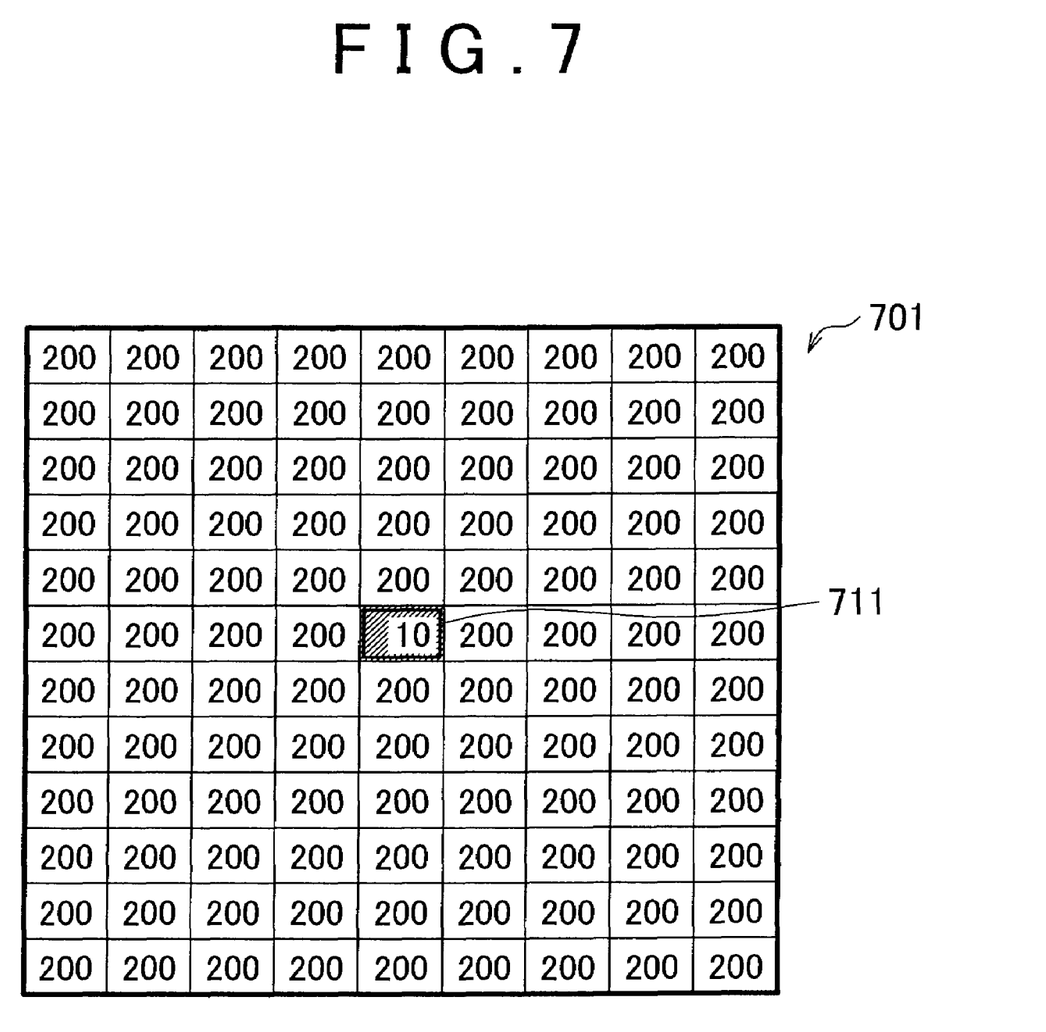
FIG. 7 is a view that illustrates the principle of the differentiation according to the embodiment of the invention.

Next, the principle of differentiation according to the embodiment of the invention will be described with reference to FIG. 7. An image 701 shown in FIG. 7 consists of 9 by 12 pixels and includes an image portion that the user wants to keep, that is, a paint defect 711. A paint defect typically spreads over a plurality of pixels; however, for the sake of easy description, the paint defect 711 occupies only one pixel. In the image 701, an image portion having a large density gradient and extending over a relatively long region as in the case of a panel edge portion is not present near the paint defect 711. The numerals shown in respective lattice cells indicate values of densities (luminances) of the pixels. Thus, the numeric value is large for a pixel having a high density, that is, a bright pixel, and the numeric value is small for a pixel having a low density, that is, a dark pixel. Here, it is assumed that the density of the paint defect 711 is 10 and the densities of the other pixels are 200.

The differentiation sequentially picks up pixels one by one from among the pixels that constitute the image 701. These are referred to as reference pixels. The density of each reference pixel is compared with the densities of pixels around that reference pixel. Here, when a difference between the density of the reference pixel and the corresponding density (average density) of the pixels around the reference density is larger than a predetermined value, it may be determined that the reference pixel is a paint defect. More specifically, when the reference pixel is the paint defect 711, a difference in density between the reference pixel and the pixels around the reference pixel is 200−10=190. Thus, it is possible to identify the paint defect 711. In this case, whichever the average value of similar densities in the close region or the average value of similar densities in the wide region is used as the density of the pixels around the reference pixel, the result is the same.

Figure 8:
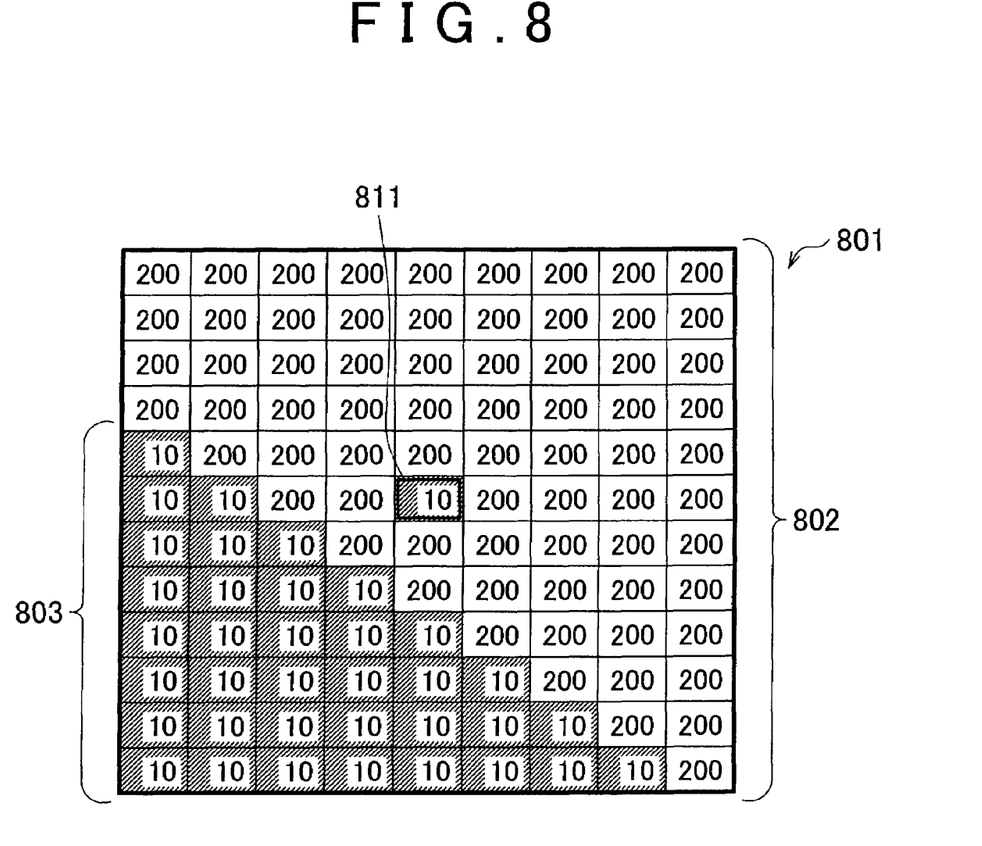
FIG. 8 is a view that illustrates the principle of the differentiation according to the embodiment of the invention.

An image 801 shown in FIG. 8 consists of a panel portion 802 and a panel edge portion 803, and includes a paint defect 811 in the panel portion 802. The paint defect 811 is present near the panel edge portion 803. The numerals shown in respective lattice cells indicate values of densities (luminances) of the pixels. Here, it is assumed that each close region Ai set in step S301 of FIG. 5 is a region consisting of 8 pixels (3 by 3 pixels) around the reference pixel, and each wide region Bi set in step S401 of FIG. 6 is a region consisting of 80 pixels (9 by 9 pixels) around the reference pixel. In addition, it is assumed that the number of pixels picked up in step S302 of FIG. 5 and step S402 of FIG. 6 is one. Thus, in step S303 of FIG. 5 and step S403 of FIG. 6, the average value of densities of picked up pixels is calculated, and this average value is the density of the one pixel picked up in the previous step.

Figure 4:
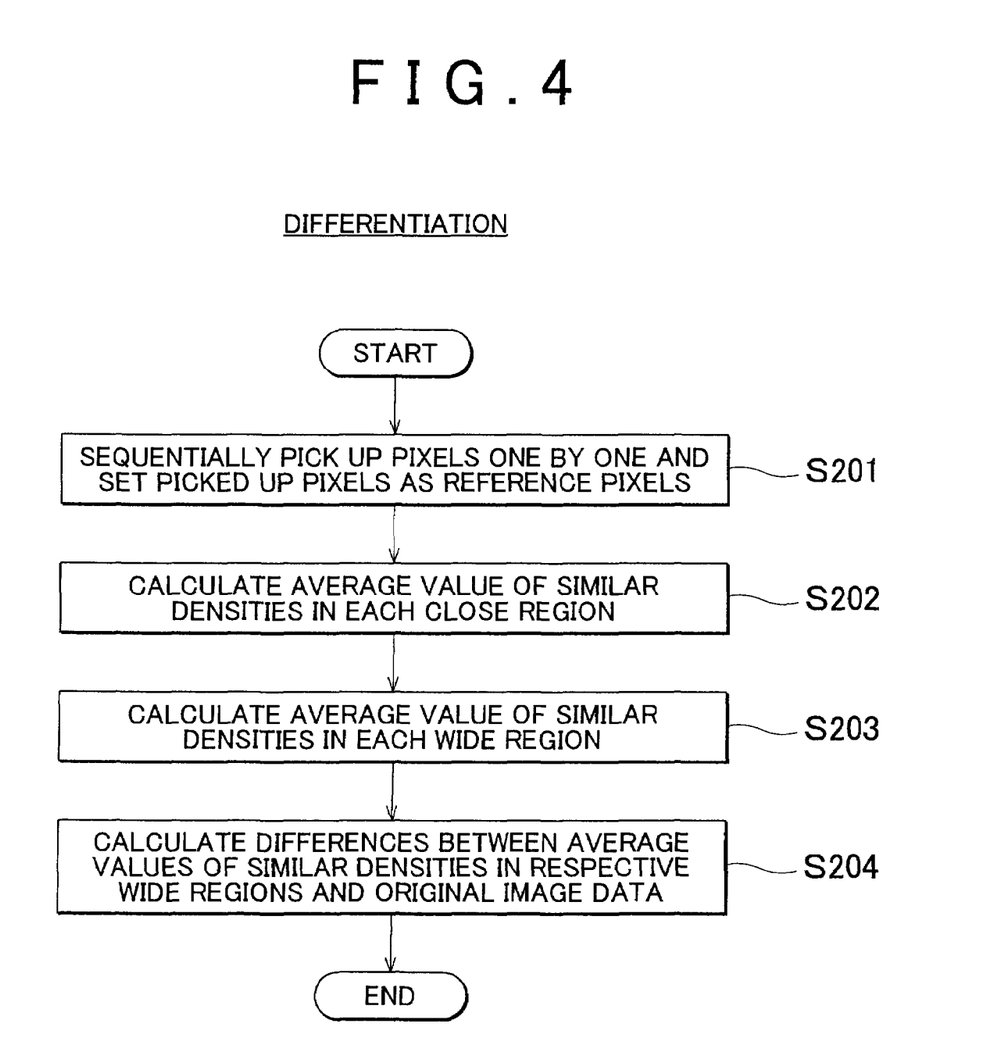
FIG. 4 is a flowchart that shows the overview of differentiation according to the embodiment of the invention.
Figure 5:
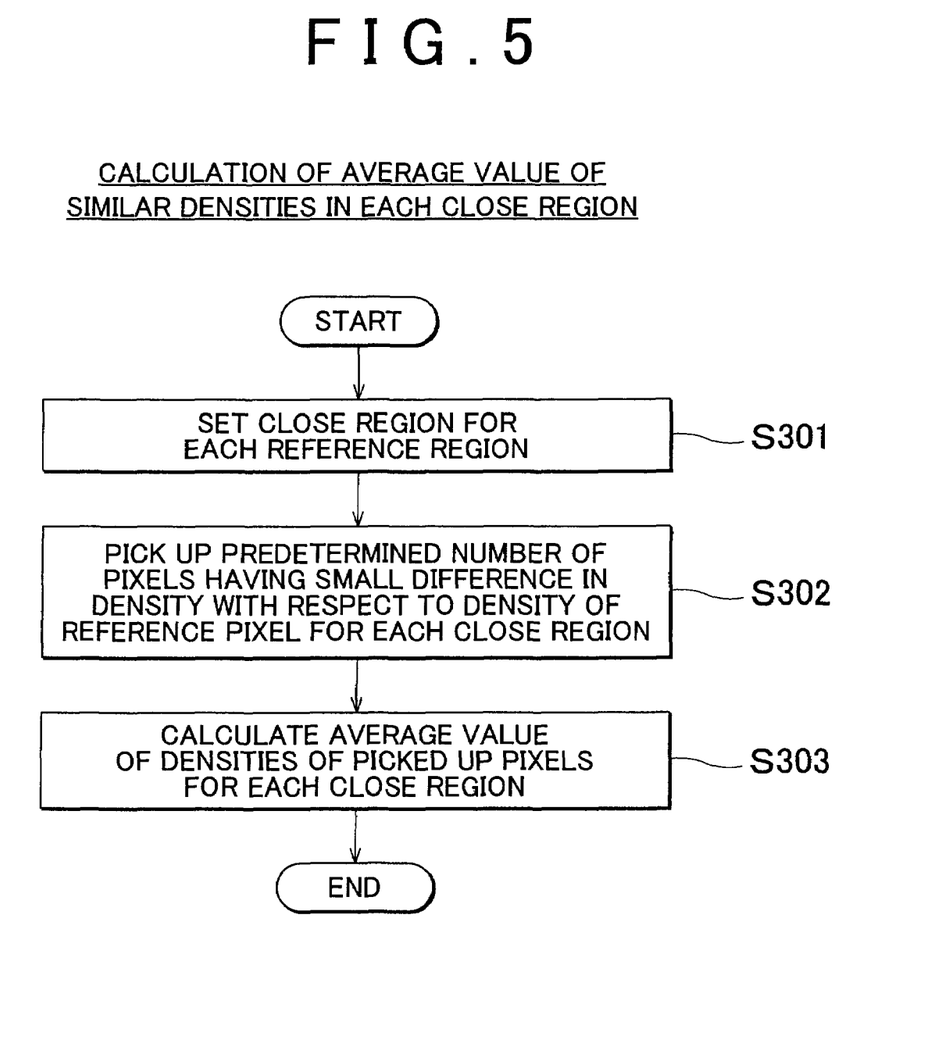
FIG. 5 is a flowchart that shows the overview of a process of calculating an average value of similar densities in each close region in the differentiation according to the embodiment of the invention.

When the reference pixel is located at the panel portion 802, an average value of similar densities in the close region, calculated in step S202 of FIG. 4, is 200. An average value of similar densities in the wide region, calculated in step S203 of FIG. 4, is 200. Thus, a difference calculated in step S204 of FIG. 4 is a difference=200−200=0.

When the reference pixel is in the panel edge portion 803, an average value of similar densities in the close region, calculated in step S202 of FIG. 4, is 10. An average value of similar densities in the wide region, calculated in step S203 of FIG. 4, is 10. Thus, a difference calculated in step S204 of FIG. 4 is a difference=10−10=0.

When the reference pixel is located at the paint defect 811, the moving average of similar densities in the close region in step S202 of FIG. 4 is 200. The moving average of similar densities in the wide region in step S203 of FIG. 4 is 200. Thus, a difference calculated in step S204 of FIG. 4 is a difference=200−10=190. Here, the moving average is a method in which the average value of values in the close region is set at the value of the reference pixel.

Thus, the difference value is large in the paint defect 811, whereas the difference value is small in the panel portion 802 and the panel edge portion 803. Therefore, the density gradient in the panel edge portion 803 is removed, and then the paint defect 811 may be detected.

Figure 9:
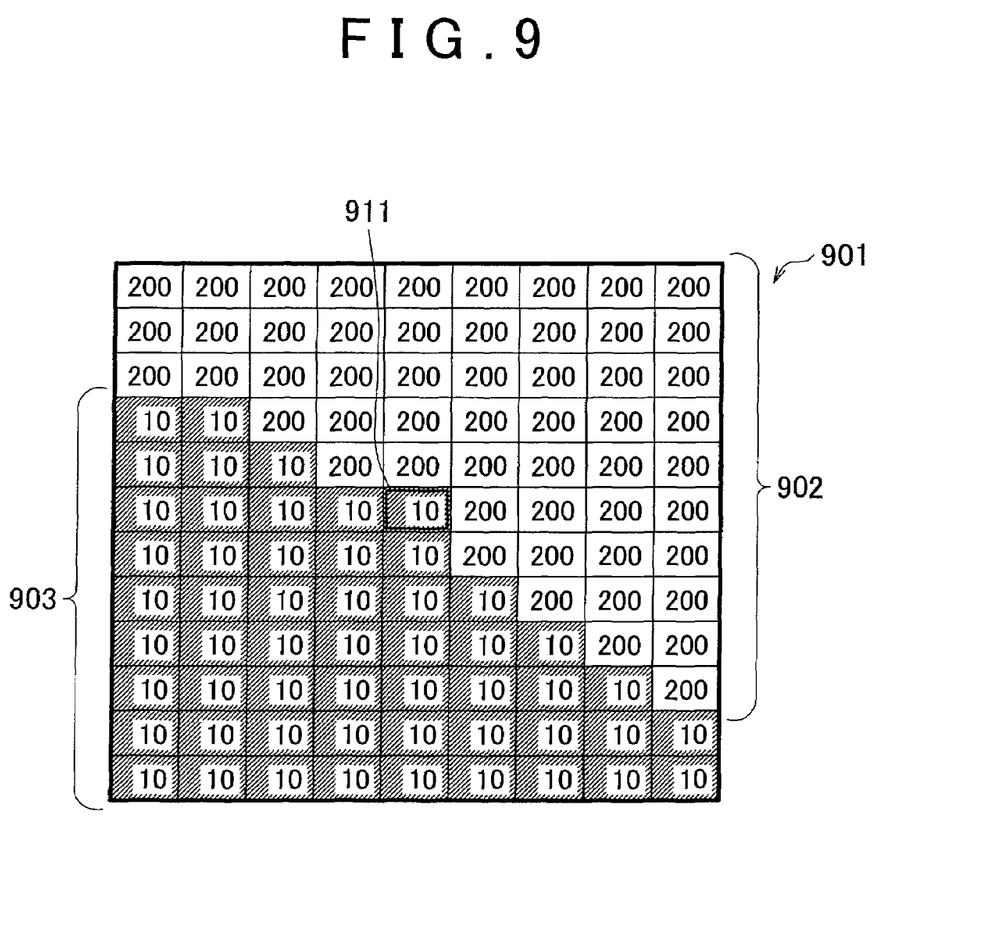
FIG. 9 is a view that illustrates the principle of the differentiation according to the embodiment of the invention.

An image 901 shown in FIG. 9 consists of a panel portion 902 and a panel edge portion 903, and a paint defect 911 adjoins the panel edge portion 903. When the reference pixel is in the panel portion 902 or in the panel edge portion 903, as in the case of the image 801 shown in FIG. 8, a difference calculated in step S204 of FIG. 4 is a difference=10−10=0. When the reference pixel is located at the paint defect 911, the moving average of similar densities in the close region in step S202 of FIG. 4 is 10. The moving average of similar densities in the wide region in step S203 of FIG. 4 is 10. Thus, a difference calculated in step S204 of FIG. 4 is a difference=10−10=0.

Thus, when the paint defect 911 adjoins the panel edge portion 903 as in the case of the image 901 in FIG. 9, it is impossible to distinguish the paint defect 911 from the panel edge portion 903. Thus, it is impossible to detect the paint defect 911.

In the differentiation according to the embodiment of the invention, it is desirable that a panel edge is not present near a paint defect. Furthermore, according to the embodiment of the invention, a density change to be removed desirably extends over a relatively wide range as in the case of a panel edge. Thus, according to the embodiment of the invention, when a paint defect is isolated away from a panel edge, it is possible to detect the paint defect and remove an image caused by a density gradient of the panel edge portion. That is, when the paint defect 911 adjoins the panel edge portion 903 as in the case of the image 901 shown in FIG. 9, it is impossible to detect the paint defect. In this case, it is only necessary that a method of setting a close region is changed.

For example, in the image 901 of FIG. 9, when the reference pixel is present at the paint defect, it is only necessary that the close region is set so as to include pixels having a density different from the density of the reference pixel and, when the average of similar densities in the close region is calculated, pixels are selected so as to include many pixels having a density different from the density of the reference pixel. For example, when the reference pixel is present at the paint defect, the close region may be set in the panel portion.

Furthermore, it is only necessary that the wide region is set so as to include pixels having a density different from the average value of similar densities in the close region and, when the average of similar densities in the wide region is calculated, pixels are selected so as to include many pixels having a density different from the average value of similar densities in the close region.

The image processing method according to the aspect of the invention may be applied to a process of detecting a paint defect by the paint inspection system for the body of a vehicle; instead, the image processing method may be applied to an image processing technique in another technical field.

While the invention has been described with reference to example embodiments thereof, it is to be understood that the invention is not limited to the described embodiments or constructions. On the other hand, the invention is intended to cover various modifications and equivalent arrangements. In addition, while the various elements of the disclosed invention are shown in various example combinations and configurations, other combinations and configurations, including more, less or only a single element, are also within the scope of the appended claims.

What is claimed is:

1. An image processing method that differentiates image data using an image processing system that includes a processing unit and a storage unit, comprising:

an image data acquisition step of acquiring image data, which include a density of each pixel acquired by an image pickup apparatus, using the processing unit;

a reference pixel acquisition step of sequentially picking up pixels one by one at a predetermined pitch from among the pixels that constitute the image data and setting the picked up pixels as reference pixels;

a close region setting step of setting a predetermined region around each of the reference pixels as a close region;

a first similar density acquisition step of picking up a predetermined number of pixels having a small difference in density with respect to the density of a corresponding one of the reference pixels in increasing order of a difference in density from among the pixels included in each close region, using the processing unit;

a first similar density average calculation step of calculating an average value of densities of the pixels picked up in the first similar density acquisition step for each of the close regions, using the processing unit;

a wide region setting step of setting a predetermined region larger than the close region around each of the reference pixels as a wide region;

a second similar density acquisition step of picking up a predetermined number of pixels having a small difference in density with respect to a corresponding one of the average values calculated in the first similar density average calculation step in increasing order of a difference in density from among the pixels included in each of the wide regions, using the processing unit;

a second similar density average calculation step of calculating an average value of densities of the pixels picked up in the second similar density acquisition step for each of the wide regions, using the processing unit; and a step of calculating a difference between the density of each of the reference pixels and a corresponding one of the average values calculated in the second similar density average calculation step, using the processing unit.

2. The image processing method according to claim 1, wherein the number of pixels included in each close region is equal among all the close regions.

3. The image processing method according to claim 1, wherein the number of pixels included in each wide region is equal among all the wide regions.

4. A paint inspection method comprising:

a step of irradiating illumination light to a vehicle body by a lighting unit;

a step of picking up a digital image of the vehicle body by an image pickup apparatus;

a step of differentiating the digital image of the vehicle body by an image processing system that includes a processing unit and a storage unit; and a step of detecting a paint defect using the differentiated image data, wherein the differentiating step includes an image data acquisition step of acquiring image data, which include a density of each pixel acquired by the image pickup apparatus, using the processing unit;

a reference pixel acquisition step of picking up pixels one by one sequentially at a predetermined pitch from among the pixels that constitute the image data and setting the picked up pixels as reference pixels;

a close region setting step of setting a predetermined region around each of the reference pixels as a close region;

a first similar density acquisition step of picking up a predetermined number of pixels having a small difference in density with respect to the density of a corresponding one of the reference pixels in increasing order of a difference in density from among the pixels included in each close region, using the processing unit;

a first similar density average calculation step of calculating an average value of densities of the pixels picked up in the first similar density acquisition step for each of the close regions, using the processing unit;

a wide region setting step of setting a predetermined region larger than the close region around each of the reference pixels as a wide region;

a second similar density acquisition step of picking up a predetermined number of pixels having a small difference in density with respect to a corresponding one of the average values calculated in the first similar density average calculation step in increasing order of a difference in density from among the pixels included in each of the wide regions, using the processing unit;

a second similar density average calculation step of calculating an average value of densities of the pixels picked up in the second similar density acquisition step for each of the wide regions, using the processing unit; and a step of calculating a difference between the density of each of the reference pixels and a corresponding one of the average values calculated in the second similar density average calculation step, using the processing unit.

5. The paint inspection method according to claim 4, wherein the number of pixels included in each close region is equal among all the close regions.

6. The paint inspection method according to claim 4, wherein the number of pixels included in each wide region is equal among all the wide regions.

7. The paint inspection method according to claim 4, wherein in the step of detecting a paint defect, if a difference between the density of the reference pixel and a corresponding one of the average values calculated in the second similar density average calculation step is larger than a predetermined value, it is determined that the reference pixel is a paint defect.

8. The paint inspection method according to claim 4, wherein in the close region setting step, when the reference pixel is present at the paint defect, the close region of that reference pixel is set so as to include a pixel having a density different from the density of that reference pixel.

9. The paint inspection method according to claim 4, wherein in the wide region setting step, when the reference pixel is present at the paint defect, the wide region of that reference pixel is set so as to include a pixel having a density different from a corresponding one of the average values calculated in the first similar density average calculation step.

10. A paint inspection system comprising:

a lighting unit that irradiates illumination light to a vehicle body;

an optical system that magnifies or reduces an image of the vehicle body;

an image pickup apparatus that picks up a digital image of the vehicle body; and an image processing system that detects a paint defect from the digital image of the vehicle body and that includes a storage unit, a processing unit and a memory, wherein the processing unit acquires image data, which include a density of each pixel, from the image pickup device and differentiates the image data, and the differentiation executed by the processing unit includes acquiring the image data which include the density of each pixel acquired by the image pickup apparatus;

sequentially picking up pixels one by one at a predetermined pitch from among the pixels that constitute the image data and setting the picked up pixels as reference pixels;

setting a predetermined region around each of the reference pixels as a close region; picking up a predetermined number of pixels having a small difference in density with respect to the density of a corresponding one of the reference pixels in increasing order of a difference in density from among the pixels included in each close region;

calculating an average value of densities of the picked up pixels as a first average value for each of the close regions;

setting a predetermined region larger than the close region around each of the reference pixels as a wide region;

picking up a predetermined number of pixels having a small difference in density with respect to a corresponding one of the first average values in increasing order of a difference in density from among the pixels included in each of the wide regions;

calculating an average value of densities of the picked up pixels as a second average value for each of the wide regions; and calculating a difference between the density of each of the reference pixels and a corresponding one of the second average values.

* * * * *